(12) United States Patent
Fitzpatrick

(10) Patent No.: US 9,913,662 B2
(45) Date of Patent: Mar. 13, 2018

(54) CLAMP

(71) Applicant: Fitzbionics Limited, Godalming, Surrey (GB)

(72) Inventor: Noel Fitzpatrick, Godalming (GB)

(73) Assignee: Fitzbionics Limited (GB)

( * ) Notice: Subject to any disclaimer, the term of this patent is extended or adjusted under 35 U.S.C. 154(b) by 0 days.

(21) Appl. No.: 14/653,495

(22) PCT Filed: Dec. 13, 2013

(86) PCT No.: PCT/GB2013/053286
§ 371 (c)(1),
(2) Date: Jun. 18, 2015

(87) PCT Pub. No.: WO2014/096788
PCT Pub. Date: Jun. 26, 2014

(65) Prior Publication Data
US 2015/0342643 A1  Dec. 3, 2015

(30) Foreign Application Priority Data

Dec. 19, 2012 (GB) .................................. 1222930.8

(51) Int. Cl.
*A61B 17/64* (2006.01)
*A61F 2/28* (2006.01)
(Continued)

(52) U.S. Cl.
CPC .............. *A61B 17/645* (2013.01); *A61F 2/28* (2013.01); *A61F 2/2846* (2013.01);
(Continued)

(58) Field of Classification Search
CPC ..... A61B 17/60–17/666; A61B 17/68–17/683; A61B 17/7014;
(Continued)

(56) References Cited

U.S. PATENT DOCUMENTS

| | | | |
|---|---|---|---|
| 5,746,741 A * | 5/1998 | Kraus | A61B 17/171 606/267 |
| 5,885,284 A | 3/1999 | Errico et al. | |
| 5,951,604 A | 9/1999 | Scheker | |
| 6,471,703 B1 * | 10/2002 | Ashman | A61B 17/7037 606/278 |
| 8,167,908 B2 * | 5/2012 | Ely | A61B 17/7049 606/250 |
| 9,050,142 B2 * | 6/2015 | Matthys | A61B 17/7035 |
| 2005/0149019 A1 * | 7/2005 | Sasing | A61B 17/7049 606/250 |
| 2008/0208257 A1 * | 8/2008 | Matthys | A61B 17/7035 606/278 |
| 2009/0259254 A1 * | 10/2009 | Pisharodi | A61B 17/7034 606/246 |

(Continued)

FOREIGN PATENT DOCUMENTS

EP  0578320  1/1994
EP  2301456  3/2011
(Continued)

OTHER PUBLICATIONS

UK Search Report, GB Patent Application No. 1222930.8, dated Nov. 6, 2013.
(Continued)

*Primary Examiner* — Jacqueline Johanas
(74) *Attorney, Agent, or Firm* — Andrus Intellectual Property Law, LLP

(57) ABSTRACT

A clamp for a linkage for linking first and second bone fasteners of a prosthesis assembly, the clamp comprising a clamp body having a first receiving portion for receiving a first component of a prosthesis assembly and a second receiving portion for receiving a second component of the prosthesis assembly, the clamp having a deflectable member which deflects from a first position to a second position when one of the first and second components is introduced to its corresponding receiving portion, wherein when the deflectable member is in the second position and the other one of the first and second components is received by the clamp, the deflectable member is engageable with said other one of the first and second components.

14 Claims, 7 Drawing Sheets

(51) Int. Cl.
  *A61F 2/42* (2006.01)
  *A61F 2/30* (2006.01)
(52) U.S. Cl.
  CPC ............ *A61F 2/4261* (2013.01); *A61B 17/64* (2013.01); *A61F 2002/285* (2013.01); *A61F 2002/2835* (2013.01); *A61F 2002/307* (2013.01); *A61F 2002/30703* (2013.01)
(58) Field of Classification Search
  CPC ...... A61B 17/7049–17/7052; Y10T 403/7064; Y10T 403/7051
  See application file for complete search history.

(56) References Cited

U.S. PATENT DOCUMENTS

| | | | | |
|---|---|---|---|---|
| 2010/0036426 A1* | 2/2010 | Mitchell | ............ | A61B 17/7005 606/264 |
| 2010/0057131 A1* | 3/2010 | Ely | ................... | A61B 17/7049 606/250 |
| 2010/0137913 A1* | 6/2010 | Khatchadourian | ....................... | A61B 17/7014 606/258 |
| 2010/0160981 A1* | 6/2010 | Butler | .................. | A61B 17/705 606/308 |
| 2010/0222822 A1* | 9/2010 | Farris | .................. | A61B 17/7004 606/264 |
| 2011/0270314 A1* | 11/2011 | Mueller | ............... | A61B 17/704 606/264 |
| 2012/0109202 A1* | 5/2012 | Kretzer | ............. | A61B 17/7049 606/248 |
| 2014/0148912 A1* | 5/2014 | Fitzpatrick | ............ | A61F 2/4261 623/21.12 |
| 2014/0309694 A1* | 10/2014 | Kretzer | ............. | A61B 17/7049 606/248 |

FOREIGN PATENT DOCUMENTS

| | | |
|---|---|---|
| GB | 2479829 | 10/2011 |
| GB | 2492213 | 12/2012 |

OTHER PUBLICATIONS

International Search Report, PCT/GB2013/053286, dated Mar. 5, 2014 date of mailing.

* cited by examiner

CLAMP

FIELD OF THE INVENTION

The invention relates to a clamp for a linkage for linking first and second bone fasteners of a prosthesis assembly for implantation in a human or animal subject. The invention also relates to prosthesis assemblies incorporating such a clamp and methods of installing prosthesis assemblies.

BACKGROUND TO THE INVENTION

The problem of bone tumours in the human population has been well known for many years and a number of treatment options are available for dealing with this problem in humans, including limb salvage surgery, sometimes involving implantation of bone replacement implants. Bone cancers are common in dogs, often occurring at the distal part of the radius. However, although bone tumours such as osteosarcomas have been known about in the animal kingdom for many years, to date there is very little option except for amputation of the limb containing the bone tumour or euthanasia. Bone replacement implants that have been used in humans are not considered suitable for use in animals as animal joint loading patterns are different. For example, implants that are used in human upper limbs are not suitable for the forelimb of a dog, as the forelimbs are weight bearing. Furthermore, there can be little or no feedback from the animal subject.

There is a need for a cost effective treatment system for treating animals with bone tumours, in particular distal radial disease, and in particular distal radial disease in canines.

SUMMARY OF INVENTION

According to a first aspect of the invention there is provided a clamp for a linkage for linking first and second bone fasteners of a prosthesis assembly, the clamp comprising a clamp body having a first receiving portion for receiving a first component of a prosthesis assembly and a second receiving portion for receiving a second component of the prosthesis assembly, the clamp having a deflectable member which deflects from a first position to a second position when one of the first and second components is introduced to its corresponding receiving portion, wherein when the deflectable member is in the second position and the other one of the first and second components is received by the clamp, the deflectable member is engageable with said other one of the first and second components.

A prosthesis for implantation at a carpal joint with adjustable and lockable linkage was described in UK patent application no. 1210557.3. The present invention provides an alternative design. The clamp of the present invention is compact and non-bulky. This provides the advantage that the clamp is less prone to protrude through the skin when implanted. The clamp of the present invention allows first and second components of a prosthesis assembly to be coupled at desired positions relative to one another, allowing for easy and efficient assembly of a multi-part assembly and for easy and efficient installation. The deflectable member provides a member to aid locking action once the first and second components have been positioned in their desired positions relative to one another by the installer. The first and second components can be coupled to or may be integral with respective first and second bone fasteners, being any fixing suitable for fastening to bone. The clamp can be used in a radial replacement prosthesis for replacing at least part or all of a radius bone, i.e. a massive bone replacement implant. Suitably, the first component is a radial component and the second component is an ulna component.

Preferably the clamp is adapted to provide a locked configuration, wherein first and second components received by the clamp are locked in position relative to one another, and an adjustable configuration, wherein the position of the first and second components relative to one another can be adjusted. The clamp allows the first and second components to be adjusted relative to one another, yet it can also be configured to retain the first and second components rigidly in a selected position relative to one another for normal use, once the assembly has been adjusted as desired. This allows the clamp to be adjustable to provide rigid fixation between the first and second components in normal use, irrespective of the relative orientations of the subject's radius and ulna. The inventor has realised that pronation and supination in the forelimb of an animal in which a radial replacement prosthesis is implanted and which has an absence of muscle attachment in this region is detrimental to the animal. A lack of such rigid fixation produces uncontrolled pronation and supination which hinders the animal from useful gait, causing great discomfort and pain in use of the limb. When implanted in a four-legged animal such as a dog, a prosthesis incorporating a clamp of the present invention prevents the forelimb from pronating or supinating, thus providing a useful treatment for distal radial disease and other conditions. The present invention provides a clamp for a radial replacement prosthesis for replacing at least part or all of a radius bone, i.e. providing massive bone replacement. The present invention is useful not only for implantation in the forelimbs of four legged animals such as dogs, but also in humans where fixation of the radius relative to the ulna may be desirable in certain situations. The present invention is particularly suitable for implantation at a subject's wrist joint. When implanted at a subject's wrist joint, the prosthesis of the present invention can be used to cause arthrodesis at the wrist joint.

Preferably the clamp provides at least one, two, three, four or five degrees of freedom of movement of the first component relative to the second component. The clamp can therefore provide rigid fixation of the radius relative to the ulna irrespective of their orientations by virtue of the multiple degrees of freedom of the first component relative to the second component due to the adjustability of the clamp. The degrees of freedom may be rotational and/or translational.

Preferably the first receiving portion is a bore. The bore may be a through-hole having first and second open ends. Suitably the bore will be shaped and dimensioned to receive the first component. Preferably the second receiving portion is a bore. The bore may be a through-hole having first and second open ends. Suitably the bore will be shaped and dimensioned to receive the second component. Suitably the second receiving portion may have an elliptical cross-section.

Preferably the clamp is rotatably and/or translationally coupleable to the first component. Preferably the clamp is rotatably and/or translationally coupleable to the second component.

Preferably the deflectable member is a crosspiece having a longitudinal axis transverse to a longitudinal axis of one of first and second receiving portions. Preferably the longitudinal axis of the crosspiece is parallel with a longitudinal axis of said other of the first and second receiving portion."

Preferably a longitudinal axis of the first receiving portion is substantially orthogonal to a longitudinal axis of the second receiving portion. Alternatively the longitudinal axis of the first receiving portion may be at a non-zero angle relative to the longitudinal axis of the second receiving portion.

Preferably the deflectable member is disposed within one of the first and second receiving portions, said one of the first and second receiving portions having an inner wall, the deflectable member having been at least partially cut out from the inner wall. Preferably the deflectable member is attached to the inner wall at first and second ends.

Preferably when the deflectable member is in the first position it protrudes into said one of the first and second receiving portions. When the deflectable member is in the second position it may protrude into said other of the first and second receiving portions.

Preferably the clamp further comprises a locking member which may be actuated to provide the locked configuration of the clamp. Preferably the locking member exerts a compressive force on said first and second components when received by the clamp. Preferably the clamp body further comprises a bore for receiving the locking member. Preferably the bore for receiving the locking member communicates with one of the first and second receiving portions such that when the prosthesis assembly is assembled and the locking member is actuated, the locking member engages the corresponding first or second component received by said one of the first and second receiving portions. Suitably the bore for receiving the locking member intersects said one of the first and second receiving portions. Preferably the bore for receiving the locking member is at least partially screw threaded and the locking member is correspondingly at least partially screw threaded. Preferably the bore for receiving the locking member has a longitudinal axis which is substantially orthogonal to the longitudinal axes of said first and second receiving portions. As such, the longitudinal axis of the bore for receiving the locking member is substantially perpendicular to the direction of insertion of the first and second components into the clamp body.

According to a further aspect of the invention there is provided a prosthesis assembly, the prosthesis assembly comprising a clamp according to the first aspect of the invention, the prosthesis assembly further comprising a first component configured to be received by the first receiving portion and a second component configured to be received by the second receiving portion.

Preferably one or both of said first and second components is a coupling member for coupling to a bone fastener. Alternatively one or both of said first and second components may be integral with a corresponding bone fastener.

Preferably one or both of said first and second component comprises a shaft or shaft portion. Preferably one or both of said first and second components is rotatably coupleable directly or indirectly to a bone fastener.

Preferably one of the first and second components comprises a shaft extending in use from a cap member, the cap member being rotatably coupleable directly or indirectly to a bone fastener. Said shaft may be integral with or rigidly coupled to the cap member in use.

Preferably the assembly is adapted to provide a locked configuration for the cap member wherein said cap member and corresponding bone fastener are in a locked position relative to one another and an adjustable configuration wherein the position of the cap member and corresponding bone fastener relative to one another can be adjusted.

Preferably the assembly further comprises a cap locking member which may be actuated to provide the locked configuration of the cap member. Preferably the cap member and corresponding bone fastener each have bores for receiving the cap locking member in use.

Preferably one of said first and second components comprises a shaft that is rigidly attachable to a corresponding bone fastener. Said shaft may be removably attachable to said corresponding bone fastener.

Preferably the assembly comprises a first bone fastener for attaching to a radius bone and a second bone fastener for attaching to an ulna bone. Preferably the first component is coupled in use or is integral with a bone fastener for attaching to a radius bone and the second component is coupled in use with a bone fastener for attaching to an ulna bone.

Preferably the deflectable member deflects from the first position to the second position when the first component is introduced to its corresponding receiving portion. Suitably the bore for receiving the locking member communicates with the first receiving portion. Suitably the second receiving portion is adjacent to the first receiving portion, separated by a wall, having an opening therein, partially covered by the deflectable member.

Preferably the prosthesis assembly provides at least one, two, three, four, five or six degrees of freedom of movement of the first bone fastener relative to the second bone fastener. The degrees of freedom are provided by the linkage incorporating said clamp.

Preferably the assembly further comprises a third bone fastener for attachment to at least one carpal bone in use. Preferably the assembly further comprises a coupling member integral with or attachable to the third bone fastener, the coupling member being rotatably coupleable to the first component. Suitably the assembly is adapted to provide a locked configuration for the coupling member wherein said coupling member and first component are in a locked position relative to one another and an adjustable configuration wherein the position of the coupling member and first component relative to one another can be adjusted.

According to a further aspect of the invention there is provided a kit for assembly into a prosthesis assembly according to the present invention, wherein the kit comprises the parts of the prosthesis assembly ready for assembly. Instructions for assembly may be provided as part of the kit.

According to a further aspect of the invention there is provided a method of installing a prosthesis assembly, the method comprising the steps of: providing a prosthesis assembly according to the present invention; introducing a first component to its corresponding first receiving portion; introducing a second component to its corresponding second receiving portion; rigidly linking the first and second components using said clamp such that the first and second components are retained substantially rigidly relative to one another. The position of the first component relative to the second component can be adjusted prior to rigidly linking the first and second components relative to one another.

According to a further aspect of the invention there is provided a computer program embodied on a computer readable medium for manufacturing a clamp or a prosthesis assembly according to the present invention. This allows the clamp or parts for the prosthesis assembly to be made via rapid manufacturing (for example via laser printing).

Features mentioned above with respect to the first aspect of the invention may be applied in any combination to the second aspect of the invention, as those skilled in the art will appreciate. Similarly, features mentioned above with respect to the second invention may be applied in any combination to the first aspect of the invention.

The term distal as used herein means located away from the centre of the subject's body when implanted and the term proximal means located near the centre of the subject's body when implanted. The term subject or patient as used herein refers to a human or animal subject. References to a locked configuration as used herein refer to a state in which movement of corresponding component parts is prevented by frictional, compression, or other forces.

BRIEF DESCRIPTION OF THE DRAWINGS

A preferred embodiment of the present invention will now be more particularly described by way of example only with reference to the accompanying drawings, wherein:

FIG. 4A is a front perspective view; FIG. 4B is a further front perspective view; FIG. 4C is a front elevation; FIG. 4D is a side elevation; FIG. 4E is a side perspective view;

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 1A:
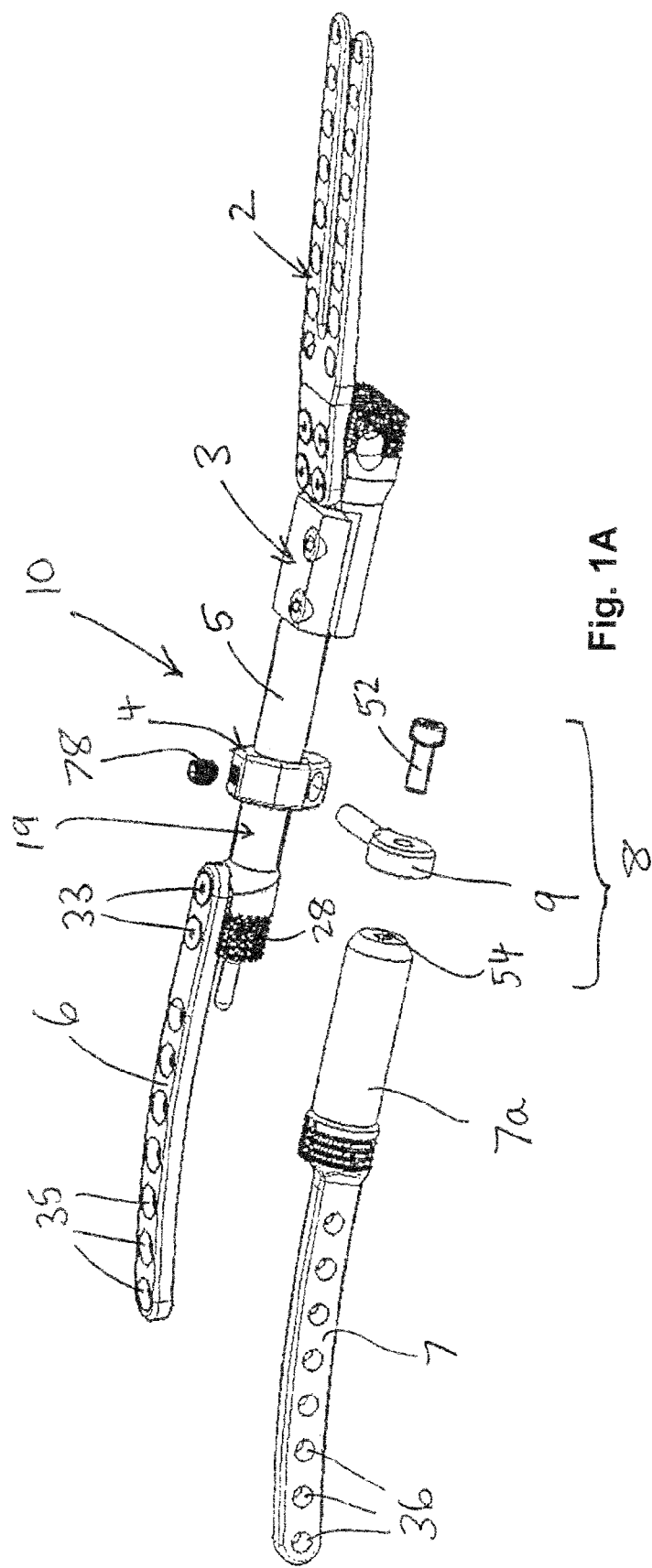
FIG. 1A is a top distal perspective view of a prosthesis assembly according to an embodiment of the invention showing the linkage partially exploded.

Referring to FIG. 1A, an endo-prosthetic assembly 10 is shown. The endo-prosthetic assembly 10 is configured for implantation at a joint, in particular a carpal joint (otherwise known as wrist joint) of a human or animal subject. The assembly comprises a first distal plate 2, a first proximal plate 6, a second proximal plate 7, and linkage 8 for linking the plates, which are shown partially exploded in FIG. 1A. The linkage 8 comprises a clamp body 4, a first component 19 and a second component 9.

Referring to FIG. 1A, the first proximal plate 6 is a curved radial plate for attachment to the radius in a wrist joint. In subjects where the distal portion of the radius bone has been resected due to distal radial disease, the first proximal plate 6 will be attached to the proximal radial bone remnant. The first proximal plate 6 is attached in use to the radial bone using bone screws (not shown), receivable through a plurality of holes 35 on plate 6. One or more bone screws can be used to secure the plate 6 to the bone as appropriate.

Figure 2:
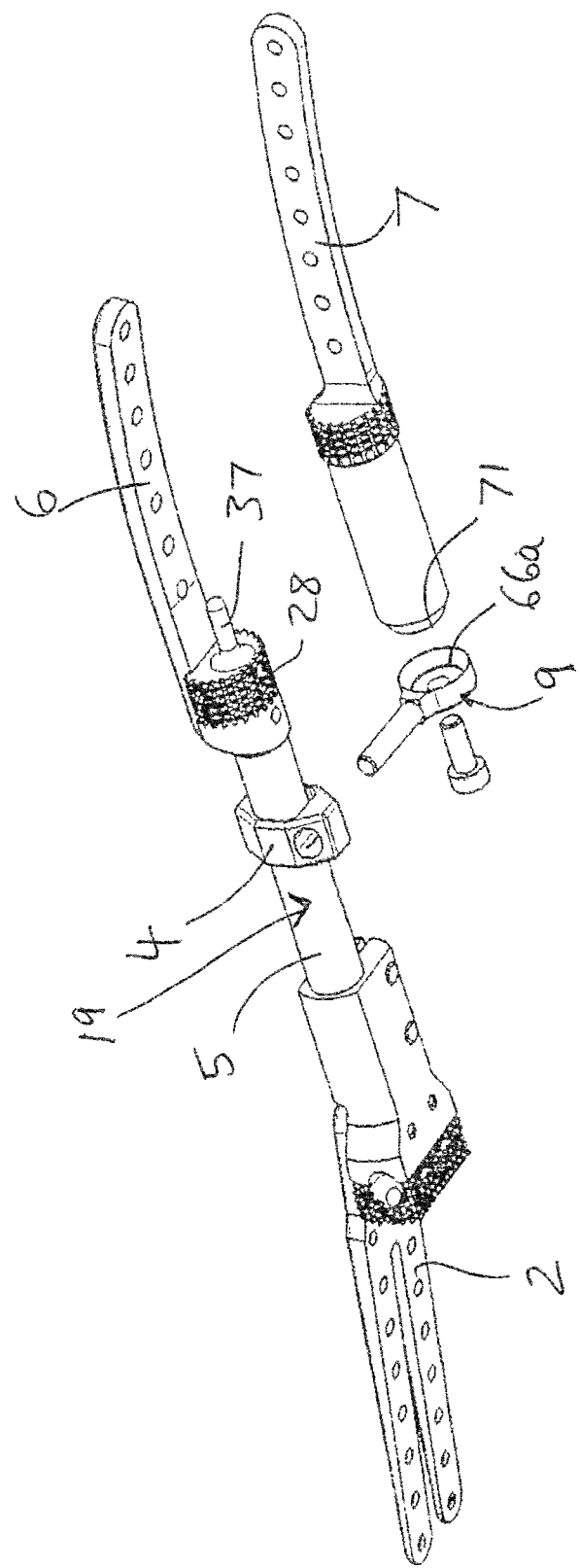
FIG. 2 is a an underside perspective view of the exploded assembly of FIG. 1A.

The first component 19 of the assembly assembles between the first proximal plate 6 and first distal plate 2 in use. The first component 19 has an enlarged portion 28 at its proximal end and an elongate shaft 5 at its distal end. The shaft portion 5 is cylindrical in shape. A curved undersurface of enlarged portion 28, which is adjacent bone when implanted, has grooves or stipples coated with hydroxyapatite to aid bone in-growth. Referring to FIG. 2, there is a short intramedullary stem 37 extending from the distal end of the enlarged portion 28, for receipt within an intramedullary cavity of the radius when implanted, to further fix the prosthesis assembly relative to the radius.

The distal end of first proximal plate 6 has two holes and the proximal end of the first component 19 has two corresponding holes (not visible in the figures), for receiving bolts 33, to rigidly secure the first proximal plate 6 to the first component 19. Alternatively, proximal plate 6 could be made in one piece with the first component 19 thus eliminating the need of bolts 33. The distal end of first proximal plate 6 seats in use in a recessed area (not visible in the figures) of an enlarged portion 28 of at the proximal end of first component 19 such that the distal end of the first proximal plate 6 is constrained by short side walls of the recess, helping to prevent the first proximal plate 6 from twisting relative to the first component 19 when assembled.

Referring to FIG. 1A, the second proximal plate 7 is a curved ulna plate for attachment to the ulna. In subjects where the distal portion of the ulna bone has been resected, the first proximal plate 7 will be attached to the proximal ulna bone remnant. The first proximal plate 7 is attached in use to the ulna bone using bone screws (not shown), receivable through a plurality of holes 36 on plate 7. One or more bone screws can be used to secure the plate 7 to the bone as appropriate.

The second proximal plate 7 has an enlarged distal portion 7a. The enlarged distal portion 7a is substantially cylindrical in shape, and includes a proximal portion having an outer surface that has grooves or stipples coated with hydroxyapatite to aid bone in-growth. The enlarged distal portion 7a may be integral with second proximal plate 7 or rigidly attached to it in use.

Figure 5:
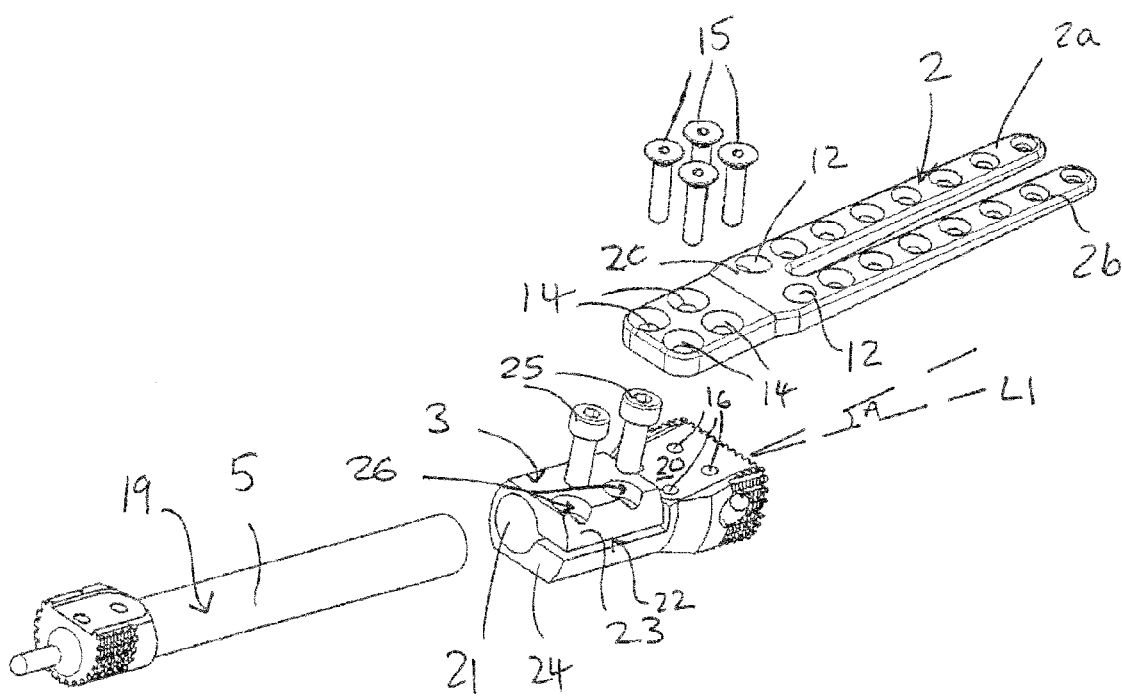
FIG. 5 is an exploded side perspective view of a distal portion of the prosthesis assembly of FIG. 1A, shown with the body component and distal plate and first component.
Figure 6:
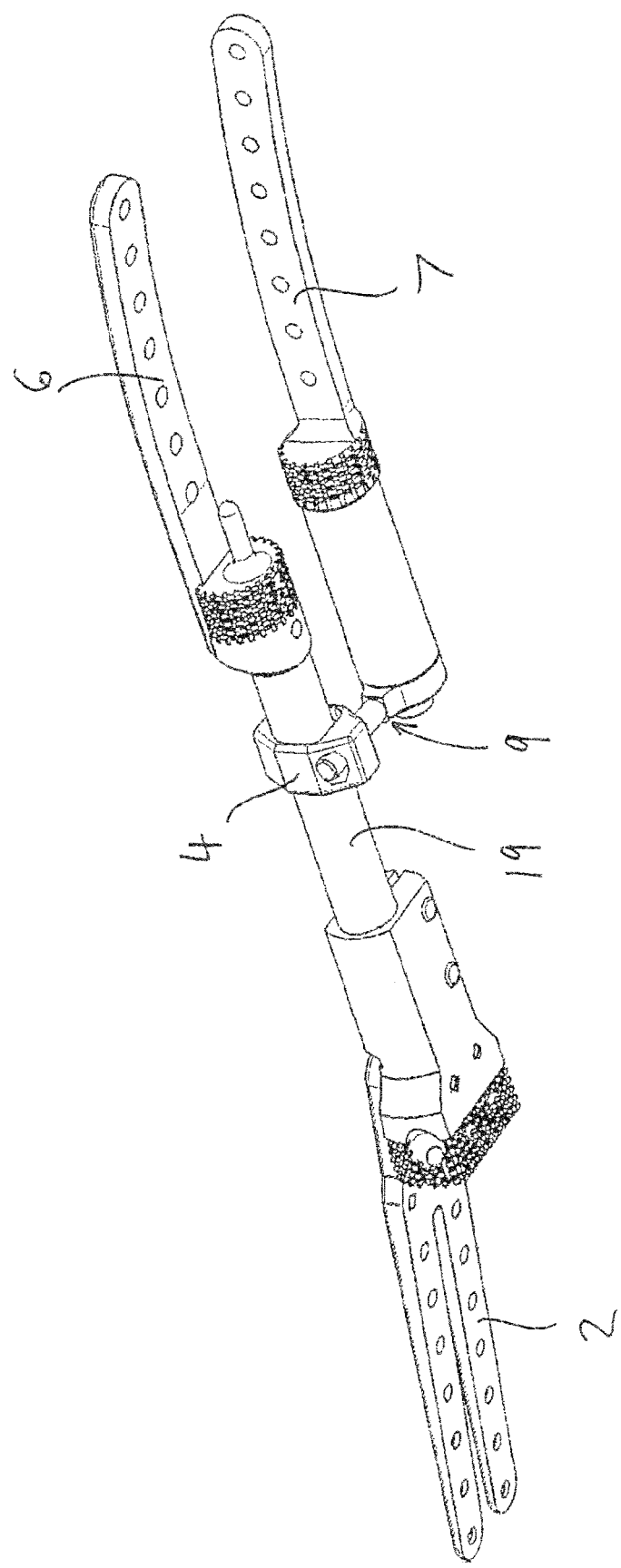
FIG. 6 is a perspective view of the prosthesis assembly of FIG. 1A, fully assembled.

Referring to FIG. 5, the first distal plate 2 is a bone fastener adapted for fixation to a bone distal of the joint. When used at the carpal joint, as in this embodiment, the first distal plate 2 is adapted for attachment to carpal bones in use. The distal plate 2 is substantially planar, having a thickness of around 2 to 7 mm. The first distal plate 2 comprises first and second elongate fingers 2a, 2b, rigidly joined at a proximal bridging portion 2c. The first and second fingers 2a, 2b extend substantially parallel with one another and fix to adjacent carpal bones of the wrist in use. The first and second fingers 2a, 2b may fix to the second and third or third and fourth metacarpal bones of the joint respectively. Each of the fingers 2a, 2b has a plurality of holes 11, each for receiving a screw or other suitable fixing, for fixing the finger to bone. The bridging portion 2c also has first and second holes 12, each for receiving a screw or other suitable fixing for fixing the first distal plate 2 to bone.

The bridging portion 2c of the first distal plate 2 includes four further holes 14, each for receiving a screw 15. The prosthesis assembly includes a body component 3 for coupling the first component 19 to the distal plate 2. The body component 3 has corresponding holes 26, each for receiving a screw 15, such that the first distal plate 2 can be rigidly secured in use to the body component 3. The body component 3 may have a hydroxyapatite coated under surface adjacent to the bone when implanted, to aid bone in-growth. The distal end of the body component 3 is grooved or stippled and may be optionally hydroxyapatite coated to further aid bone in-growth.

The body component 3 has a surface 20 that is sloped relative to the longitudinal axis L1 of the throughbore 21 by a fixed angle A. In this embodiment the fixed angle A is 10 degrees, however the fixed angle A may have other values, preferably being greater than 0 degrees and less than 20 degrees. The proximal end of the first distal plate 2 attaches securely and rigidly to the body component 3 in use, by means of screws 15. The distal end of the first distal plate 2 is planar and lies against sloped surface 20 when assembled, such that the longitudinal axis of the first distal plate 2 is offset by angle A relative to the longitudinal axis L1 of the throughbore of body component 3.

Referring to FIG. 5, the body component 3 has a throughbore 21 that extends from the proximal end to the distal end of the component. The throughbore 21 has an open end in the proximal end of the component. The body component 3 has an elongate slot 22 having an elongate axis parallel with throughbore 21, the slot 22 communicating with throughbore 21 and having an elongate opening at one side of the body component 3. The body component 3 has first and second overlapping clamping portions 23,24 above and below the slot, the clamping portions extending perpendicularly away from the longitudinal axis of the throughbore 21. The first clamping portion 23 has two through holes 26 and the second clamping portion 23 has two corresponding through holes 27, for receiving first and second bolts 25 (or other suitable fixing means) for clamping the first and second clamping portions 23, 24 tightly together. In this way, the body component 3 forms a type of clevis ring that can clamp around the shaft 5 by means of bolts 25.

Figure 1B:
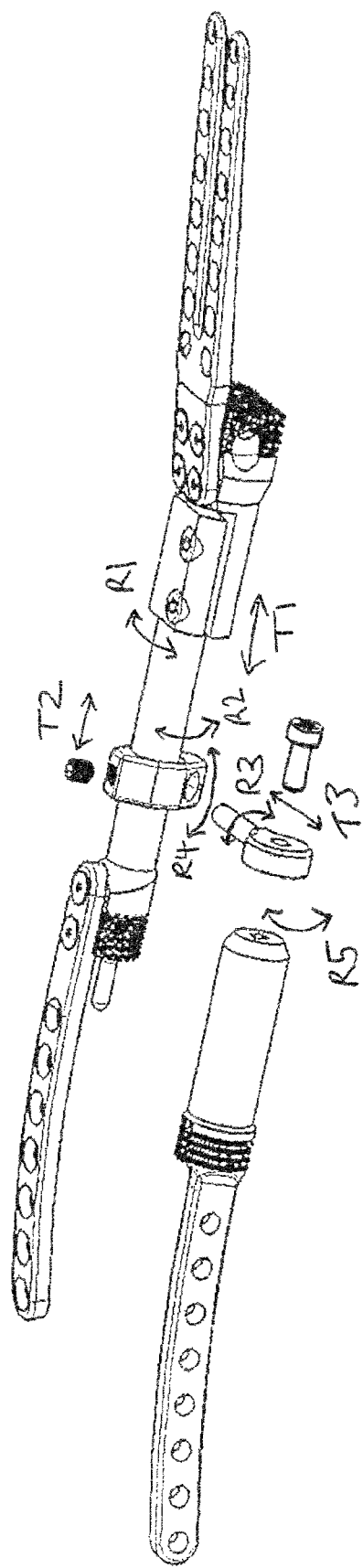
FIG. 1B is the same view of the assembly as FIG. 1A, included to indicate degrees of freedom of the assembly.

When the first and second clamping portions 23, 24 are not clamped tightly together the distal end of first component 19 can be inserted in the proximal end of the body component 3, and the first component 19 can be rotated relative to the body component 3 within throughbore 21. This arrangement allows rotational adjustment of the first proximal plate 6 relative to the distal plate 2 and vice versa during implantation, such that the assembly is configured for stable attachment to at least two bones of the subject, irrespective of variations in anatomy between subjects. This allows for pronation/supination adjustment of the distal plate 2 relative to the first proximal plate 6 during implantation to reach the desired orientation between the first proximal plate and first distal plate. Referring to FIG. 1B, this arrangement provides a rotational degree of freedom R1 of the shaft 5 (and therefore the first proximal plate 6 to which the shaft 5 is rigidly assembled in use) relative to the body component 3 (and therefore to the distal plate 2, to which the body component is rigidly assembled in use). Furthermore, when the first and second clamping portions 23, 24 are not clamped tightly together the distal end of shaft 5 can be adjusted back and forth within the body component 3 (i.e. the distal end of shaft 5 can telescope within throughbore 21). The bolted clamp arrangement around shaft 5 allows for adjustment of the overall length of the assembly, and therefore adjustment of the length between the proximal end of first proximal plate 6 and the distal end of distal plate 2 during implantation. This arrangement provides a translational degree of freedom T1 of the first component 19 (and therefore the first proximal plate 6 to which the first component 19 is rigidly assembled in use) relative to the body component 3 (and therefore to the distal plate 2, to which the body component 3 is rigidly assembled in use). Once the first and second clamping portions 23, 24 have been clamped tightly together using bolts 25, the distal end of shaft 5 is rigidly held in throughbore 21, and is not able to rotate or move translationally with respect to body component 3.

The linkage 8 that links the second proximal plate 7 with the first proximal plate 6 (and therefore also with the first distal plate 2 if included in the assembly) in use will now be further described. The linkage 8 comprises a clamp body 4, a first component 19 and a second component 9.

The second component 9 comprises a cap member 65 and a shaft portion 67 which extends away from the cap member 65. The cap member 65 is circular in shape, the shaft portion 67 extending along a longitudinal axis parallel with the plane of the circular shaped cap member 65.

Referring to FIGS. 4A to 4E, the clamp body 4 has a first bore 72 for receiving the shaft 5 and a second bore 74 for receiving the second component 9. Suitably, the first bore 72 is a throughbore, shaped and dimensioned to receive the cylindrical shaft 5 and the second bore 74 is a throughbore, shaped and dimensioned to receive a cylindrical portion of second component 9. The height h1 of the first bore 72 substantially matches or is slightly larger than that of the diameter of the shaft 5. The height h2 of the second bore 74 substantially matches the diameter of the shaft portion 67 of the second component 9, such that there is a tight fit when the second component is installed in the clamp body 4. The cross-sectional shape of the second bore 74 is elliptical, having a width w2 which is larger than its height h2.

The clamp body 4 includes a deflectable member 70 cutaway from the inner wall of the clamp body that partitions the first bore 72 from the second bore 74. The deflectable member 70 is a beam or crosspiece that extends transversely across the longitudinal axis of the first bore 72. The deflectable member 70 is attached to an inner wall of the clamp body 4 at first and second ends 70a of the deflectable member, allowing the mid-portion of the deflectable member 70 between the ends to deflect resiliently. There are slots 79, on either side of the deflectable member 70, in the inner wall of the clamp body that partitions the first bore 72 from the second bore 74. By means of the deflectable member 70 having been carved out of the inner wall of the clamp body that partitions the first bore 72 from the second bore 74 with attachments at first and second ends, the deflectable member 70 effectively sits covers an aperture in the inner wall.

Figures 4C, 4D:
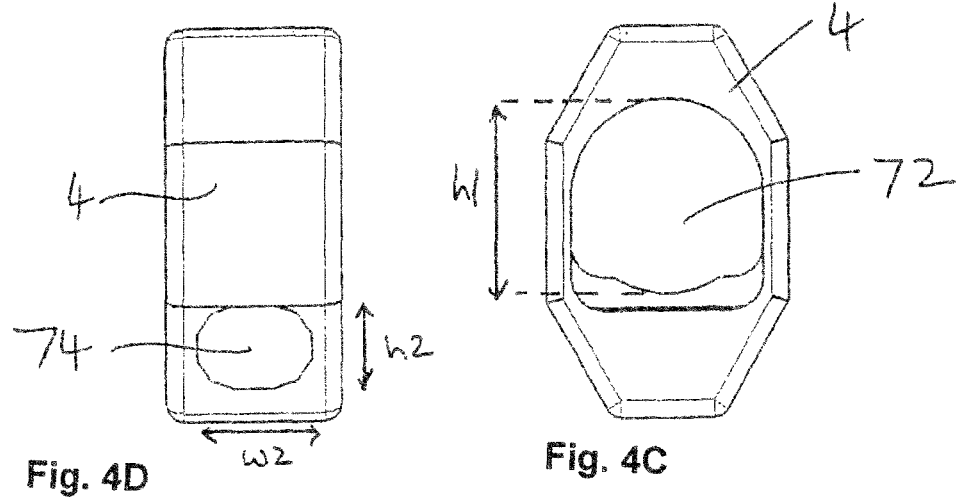
FIGS. 4A to 4E show views of the clamp body.
Figures 4A, 4B:
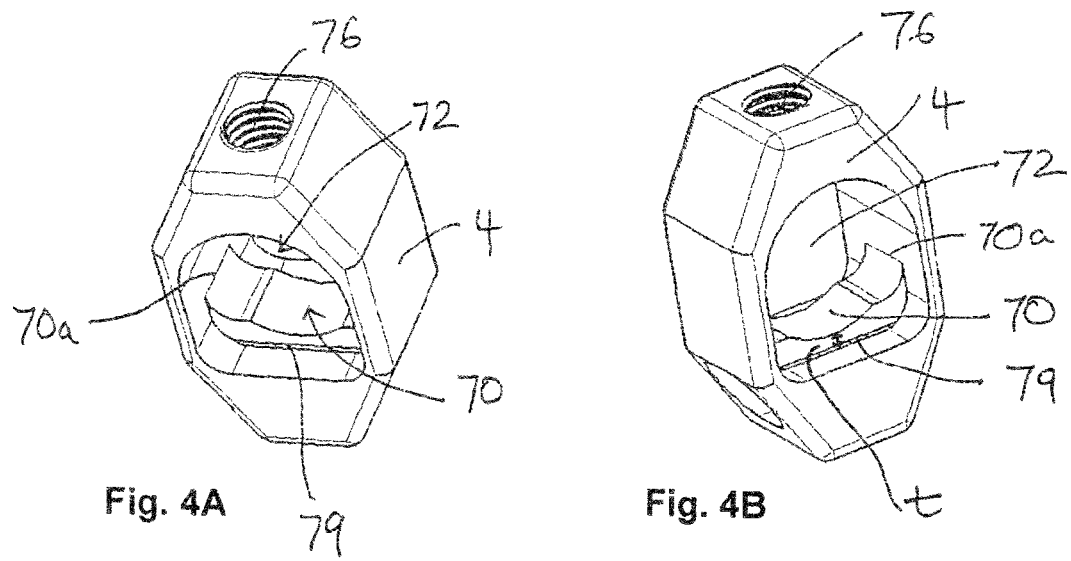
Figure 4E:
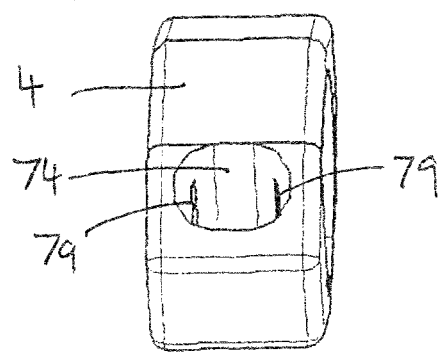

The deflectable member 70 is deflectable between a first position, wherein it protrudes into the first bore 72 (as shown in FIGS. 4A, 4B and 4C) and a second position wherein it would engage a shaft inserted in the second bore 74. When the deflectable member 70 is in the second position it may protrude into the second bore 74. Preferably the deflectable member 70 has a thickness t at its mid-portion of around 1 mm, and is thicker at both ends, allowing the mid-portion to resiliently deflect in use. Preferably the deflectable member 70 has a thickness of around 2 mm at its first and second ends 70a, where it attaches to the inner wall.

Figure 3:
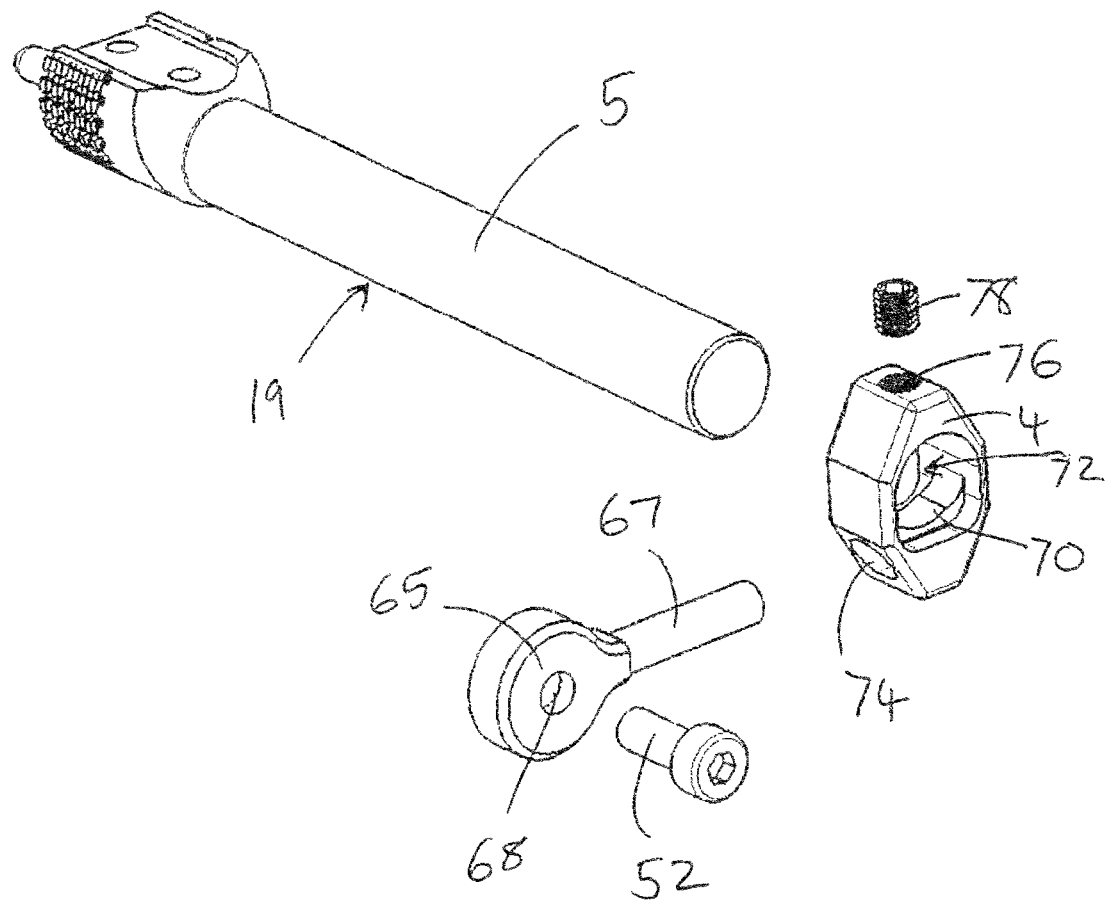
FIG. 3 is a distal perspective view of the clamp, first component and second component of the FIG. 1A assembly, exploded from one another.

Referring to FIG. 3, the clamp body 4 has a third throughbore 76 for receiving a locking member 78. Locking member 78 can be any suitable locking means for applying a compressive force on the first component 19 and second component 9 when received in the clamp body 4. In this particular embodiment, locking member 78 is a grub screw, which is externally threaded, such that it engages with corresponding internal threading in the third bore 76 when installed. When actuated to clamp the first component 19 and second component 9 against movement relative to clamp body 4, the locking member 78 provides a locked configuration. When the clamp body 4, first component 19 and second component 9 are assembled but not locked rigidly using the locking member 78, the assembly is in an adjustable configuration (for example if the locking member 78 is not inserted within bore 76 or is not inserted to a full enough extent to provide the locked configuration).

Insertion of the shaft 5 into the first bore 72 causes the deflectable member 70 to deflect from its first position, wherein it protrudes into the first bore, into its second position. When shaft portion 67 is received by bore 74 and the deflectable member 70 is in the second position, the deflectable member engages the shaft portion 67. The deflectable member 70 need not protrude into the second bore 74 when in the second position; as long as the height h2 of the second bore 74 substantially matches the diameter of the shaft portion 67, the deflectable member 70 will engage the shaft portion 67 when the deflectable member 70 is in the second position. When the locking member 78 is actuated to provide the locking configuration, the locking member exerts a compressive force on said shaft 5 received in the first bore 72. This compressive force is transferred, via the deflectable member that effectively spans an aperture in the wall partitioning the first bore 72 and second bore 74, to the shaft portion 67 received in the second bore 74. This compresses the shaft portion 67 against the bottom wall of second bore 74, thus clamping the first component 19 and second component 9 rigidly with the clamp body.

The cap member 65 of the second component 9 attaches to the distal end of the second proximal plate 7 in use, using screw 52, which passes through a hole 68 in the cap member and into a bore 54 in the distal end of the second proximal plate 7. Preferably screw 52 is externally threaded, the bore 54 being correspondingly internally screw threaded, such that the screw can be threadedly engaged in bore 54. The cap member 65 can be rigidly and non-movably engaged with the second proximal plate 7 by means of a friction engagement by the action of the head of screw 52 clamping the cap member 65 against the distal end of the second proximal plate 7. Screw 52 may be any other suitable fixing means, such as a bolt.

When assembled, the shaft 5 of first component 19 passes through the first bore 72 of clamp body 4 and the shaft portion 67 of second component 9 passes through the second bore 74. When the locking member 78 is not being used to rigidly engage the components of the linkage 8 in a locked configuration (i.e. when in the adjustable configuration), the clamp body 4 can move translationally, back and forth along shaft 5. Referring to FIG. 1B this arrangement provides a translational degree of freedom T2 of the clamp body 4 with respect to the shaft 5. When in the adjustable configuration the clamp body 4 can also move rotationally around shaft 5. This arrangement provides a rotational degree of freedom R2 of the clamp body 4 with respect to the shaft 5. When in the locked configuration, the clamp body 4 is restrained from moving translationally or rotationally relative to the shaft 5.

When the locking member 78 is not being used to rigidly engage the components of the linkage 8 in a locked configuration (i.e. when in the adjustable configuration), the shaft portion 67 of the second component 9 can move rotationally within second bore 74 of the clamp body 4. This arrangement provides a rotational degree of freedom R3 of the clamp body 4 with respect to the shaft portion 67. The shaft portion can also twist within elliptical bore 74, in a plane parallel with width w2 of second bore 74. This provides a restricted rotational degree of freedom R4. The shaft portion 67 can also move translationally back and forth relative to the clamp body 4. This arrangement provides a translational degree of freedom T3. When in the locked configuration, the shaft portion 67 (and therefore the second component 9) is restrained from moving translationally or rotationally relative to the clamp body 4.

When screw 52 is not tightly engaging the cap member 65 against the second proximal plate 7 (i.e. the cap member 65 is only loosely held against the second proximal plate 7), the cap member 65 (and therefore the second component 9) can rotate relative to the second proximal plate 7. This arrangement provides a rotational degree of freedom R5. When the cap member 65 is tightly engaged against the distal end of the second proximal plate 7 using screw 52, the second proximal plate 7 is retrained from moving rotationally relative to the second component 9.

As will be understood from the above, the linkage 8 allows for easy adjustment of the bone attachment plates 2, 6, 7 relative to one another, which assists when installing the prosthesis.

In operation, in order to install the assembly, each bone attachment plate 2, 6, 7 may be attached to the corresponding bone, and then the individual parts of the assembly assembled together, using the adjustable linkage 8 and the adjustable coupling of the first component 19 within the body component 3 to allow the individual parts of the assembly to couple with one another irrespective of the subject's anatomy.

In a preferred installation method for installation at the wrist, the first proximal plate 6, the second proximal plate 7 and the distal plate 2 are each attached to corresponding bones, then a distal assembly (comprising the distal plate 2 and body component 3) is coupled to a first proximal assembly (comprising the first proximal plate 6 and first component 19 assembled thereto, with clamp body 4 assembled to the first component 19), then the first component 19 and second proximal plate 7 are linked together using the second component 9, as will be described further below. In this preferred installation method, the distal end of the first component 19 is inserted into the first bore 72 of the clamp body 4 to assemble the clamp body 4 to the first component 19. The first component 19 is attached to the first proximal plate 6. The first proximal plate 6 is offered to the radius, the second proximal plate 7 is offered to the ulna and the first distal plate 2 is offered to carpal bones and each is oriented relative to the respective bone until it is located on a part of the bone that is optimal for fixation of bone screws thereto and then fixed to the respective bone using screws. The body component 3 may be attached to the distal plate 2 before or after the distal plate 2 is attached to bone. The first component 19 is then inserted in the throughbore 21 of body component 3. The adjustable coupling of the first component 19 with the body component 3 is adjusted as desired using one or more degrees of the freedom R1, T1 to provide a suitable length and desired rotational orientation between the first proximal plate 6 and distal plate 2. The body component 3 is then rigidly fixed to first component 19 using bolts 25 so that the first component 19 and body component 3 can no longer move relative to one another. The linkage 8 is then further assembled by inserting the shaft portion 67 of the second component 9 in second bore 74 of the clamp body 4 and loosely attaching the second component 9 to the distal end of second proximal plate 7. The linkage 8 is adjusted using one or more of the degrees of freedom T2, T3, R2, R3, R4, R5 as necessary to adjust linkage 8 before tightly engaging the locking member 78 against the clamp body 4 to convert to the locked configuration, thus non-movably fixing the clamp body 4 to first component 19 and second component 9. Following suitable adjustment the second component 9 is also fixed non-movably relative second distal plate 7. In this way, the radius and ulna can be linked by virtue of the six degrees of freedom of the linkage assembly, irrespective of the orientation of the bones in the subject.

Alternatively, the prosthesis is assembled, but with each of the couplings, each having a degree of freedom T1, T2, T3, R1, R2, R3, R4, R5 as described above, being loosely coupled. Each of the bone attachment plates 2, 6, 7 is attached to the corresponding bone and then each of the couplings (i.e. the linkage 8 couplings having degrees of freedom T2, T3, R2, R3, R4, R5 for adjustment of the linkage 8 and the coupling of the first component 19 with the coupling body 3 having degrees of freedom T1, R1) are tightened such that all parts of the prosthesis assembly are held substantially rigidly with respect to rest of the prosthesis assembly.

Once the assembly is assembled and rigid, the bone attachment plates 2, 6, 7 are fixed with respect to one another so that they cannot move with respect to one another. This causes arthrodesis of the joint. When the prosthesis assembly is fully implanted and made rigid, the distal bones of the joint will be held at a fixed angle A relative to the proximal bones of the joint, due to the extension of the distal plate 2 obliquely relative to the first proximal plate 6.

Once the assembly is assembled and rigid, the linkage 8 provides rigid fixation of the first proximal plate 6 relative to the second proximal plate 7. Where the assembly is implanted at the wrist joint, this effectively provides rigid fixation of the radius relative to the ulna, preventing pronation and supination of the limb. The linkage provides such fixation of the radius relative to the ulna irrespective of their orientations by virtue of the multiple degrees of freedom of the linking components using modular connections.

Referring to FIG. 2, the distal end 71 of the second proximal plate 7 is conical shaped, providing the distal end with a taper. The cap member 65 has a proximal side 66a that faces the distal end 71 of the second proximal plate 7 when assembled. The proximal side 66a has a corresponding internal taper to that of the distal end 71 of the second proximal plate 7 and fits over the tapered distal end 71 when installed. The tapered engagement of the cap member 65 over the distal end 71 of the second proximal plate 7 provides taper-locking, to prevent the cap member 65 from working loose, even if subjected to substantial torque forces. Preferably the taper has a shallow angle of around 20°.

Variations of the present assembly can be used, for example the deflectable member could protrude into the second bore 74 when in the first position.

It will be understood that instead of having a first distal plate 2 with first and second fingers for attaching to adjacent carpal bones, the assembly may have separate first and second distal plates for attachment to adjacent carpal bones, each plate being attachable to the body component 3. Furthermore, it is not necessary that the assembly attaches to two bones distal to the assembly when implanted; instead, the assembly may have just a first distal plate that fixes to one distal bone. Alternatively, the assembly need not include the distal plate 2 with body component 3, and may simply include the first and second proximal plates 6, 7 and linkage 8 for use in linking a subject's radius and ulna only.

The whole of the prosthesis assembly or some parts of the prosthesis assembly of any of the embodiments described herein may be made of titanium alloy, stainless steel alloy or polyetheretherketone (PEEK), with or without carbon fibres embedded therein.

Each of the bone plates 2, 6, 7 may have a hydroxyapatite coated under surface adjacent to the bone when implanted, to aid bone in-growth.

Each of the bone attachment plates 2, 6, 7, may be attached to intact bone or the remaining portion of a bone after resection of the bone.

It will be understood that instead of having bone attachment plates, the assembly may have other bone fixing means, each fixing means being any suitable means for fixation to bone, such as a bone receiving socket or an intramedullary rod.

The endo-prosthetic assembly 10 is particularly suitable for implantation at a carpal joint in a human or animal subject, as described above. However, it will be understood that the assembly could be used at other sites in the human or animal skeleton. For example, the assembly could be used as a mid-radial replacement prosthesis.

It will be understood that the prosthesis assembly is a modular assembly. Each part of the assembly can be substituted with a modified part to suit the particular anatomy at the site of implantation. The assembly can be provided as a modular kit in which a range of lengths and/or shapes for each bone fixation plate 2, 6, 7 can be provided so that the optimum length/shape plate to suit a particular subject's bone can be selected.

In the prosthesis assembly 10, the first component 19 with enlarged end 28 and the second proximal plate 7 with enlarged distal portion 7a are each single integral pieces. However, it will be understood that these components, and the other components of the assembly may each comprise two or more parts that assemble together.

The invention claimed is:

1. A clamp for a linkage for linking first and second bone fasteners of a prosthesis assembly, the clamp comprising a clamp body having a first receiving portion for receiving a first component of a prosthesis assembly and a second receiving portion for receiving a second component of the prosthesis assembly, the clamp having a deflectable member which deflects from a first position to a second position when one of the first and second components is introduced to its corresponding receiving portion, wherein when the deflectable member is in the second position and the other one of the first and second components is received by the clamp, the deflectable member is engageable with said other one of the first and second components, wherein the deflectable member is disposed within one of the first and second receiving portions when in its first position, said one of the first and second receiving portions having an inner wall, the deflectable member having been at least partially cut out from the inner wall, the deflectable member being a cross-piece having first and second ends, a mid-portion, and a longitudinal axis transverse to a longitudinal axis of the first receiving portion and parallel with a longitudinal axis of the second receiving portion, and the deflectable member being attached to the inner wall at its first and second ends, the deflectable member being configured such that its mid-portion is deflectable resiliently between the first and second positions, the first and second receiving portions being bores, each having a closed cross-sectional circumference and wherein the second receiving portion has an elliptical cross-section.

2. A clamp according to claim 1, wherein the clamp is adapted to provide a locked configuration, wherein first and second components received by the clamp are locked in position relative to one another, and an adjustable configuration, wherein the position of the first and second components relative to one another can be adjusted.

3. A clamp according to claim 1, wherein the clamp provides at least one, two, three, four or five degrees of freedom of movement of the first component relative to the second component.

4. A clamp according to claim 1, wherein the clamp is rotatably coupleable to the first component, the clamp is translationally coupleable to the first component, or the clamp is both rotatably and translationally coupleable to the first component.

5. A clamp according to claim 1, wherein the clamp is rotatably coupleable to the second component, the clamp is translationally coupleable to the second component, or the clamp is both rotatably and translationally coupleable to the second component.

6. A clamp according to claim 1, wherein the longitudinal axis of the first receiving portion is substantially orthogonal to the longitudinal axis of the second receiving portion.

7. A clamp according to claim 1, wherein when the deflectable member is in the first position it protrudes into said one of the first and second receiving portions.

8. A clamp according to claim 7, wherein when the deflectable member is in the second position it protrudes into said other of the first and second receiving portions.

9. A clamp according to claim 1, wherein the clamp further comprises a locking member which is capable of being actuated to provide the locked configuration of the clamp.

10. A clamp according to claim 9, wherein when actuated the locking member exerts a compressive force on said first and second components when received by the clamp, wherein the clamp body further comprises a bore for receiving the locking member, the bore communicating with one of the first and second receiving portions such that when the prosthesis assembly is assembled and the locking member is actuated, the locking member engages the corresponding first or second component received by said one of the first and second receiving portions, the bore for receiving the locking member being at least partially screw threaded and the locking member being correspondingly at least partially screw threaded.

11. A prosthesis assembly, the prosthesis assembly comprising a clamp according to claim 1, the prosthesis assembly further comprising a first component configured to be received by the first receiving portion and a second component configured to be received by the second receiving portion.

12. A prosthesis assembly according to claim 11, wherein each of said first and second components is a coupling member for coupling to a bone fastener.

13. A prosthesis assembly according to claim 12, wherein the first component is coupled in use or is integral with a bone fastener for attaching to a radius bone and the second component is coupled in use with a bone fastener for attaching to an ulna bone.

14. A prosthesis assembly according to claim 13, wherein the deflectable member deflects from the first position to the second position when the first component is introduced to its corresponding receiving portion.

\* \* \* \* \*